United States Patent [19]

Salia-Munoz

[11] Patent Number: 4,505,545
[45] Date of Patent: Mar. 19, 1985

[54] APPARATUS FOR APPLYING LIGHT THROUGH AN OPTICAL GRID

[76] Inventor: Miguel Salia-Munoz, 7a. Privada de Azafran 14 Col., Granjas Mexico, Mexico

[21] Appl. No.: 459,950

[22] Filed: Jan. 21, 1983

[30] Foreign Application Priority Data

Aug. 27, 1982 [MX] Mexico ................ 194194

[51] Int. Cl.³ ............... G02B 27/00; A61N 5/00
[52] U.S. Cl. .................. 350/321; 128/395; 350/322
[58] Field of Search ............ 350/321, 322, 1.1; 362/290, 293, 343; 128/395, 396, 362

[56] References Cited

U.S. PATENT DOCUMENTS

| | | | |
|---|---|---|---|
| 1,123,417 | 8/1968 | Sjolander | 362/342 |
| 1,331,422 | 2/1920 | Donaldson | 362/290 |
| 1,557,548 | 2/1969 | Electriska | 362/342 |
| 4,222,094 | 9/1980 | Wolar | 362/290 |

FOREIGN PATENT DOCUMENTS

| | | | |
|---|---|---|---|
| 1047376 | 12/1958 | Fed. Rep. of Germany | 128/395 |
| 678151 | of 1929 | France | 362/290 |

OTHER PUBLICATIONS

G-E Themospectral lamp ad. Pub. 7, p–315, 4 pp., Apr. 1938.

*Primary Examiner*—Jon W. Henry
*Attorney, Agent, or Firm*—Darby & Darby

[57] ABSTRACT

An apparatus for the application of light energy comprises a light source, a housing for said light source, a reflector at the bottom of said housing and an optical grid having frustopyramidal square openings, arranged as a cover at the opposite open end of the housing. Optionally a light filter and a flexible chamber may be provided in the apparatus, said light filter being located between the light source and the optical grid, and said flexible chamber being provided at the open end of the housing, so as to permit the application of light of predetermined frequencies and a vacuum to the surface where said light is applied.

The use of said apparatus in the application of light of several frequencies, causes certain stimulations and provides a new instrument for the treatment of certain cutaneous, muscular and nervous deficiencies. By means of the application of certain light frequencies, a germicidal action is also obtained.

3 Claims, 3 Drawing Figures

4,505,545

APPARATUS FOR APPLYING LIGHT THROUGH AN OPTICAL GRID

FIELD OF THE INVENTION

The present invention refers to an apparatus for applying light energy and, more particularly it is related to an apparatus for applying light energy of various frequencies, through an optical grid having frustopyramidal square openings, in order to accomplish certain stimulating or germicidal effects.

BACKGROUND OF THE INVENTION

Various methods for providing stimulation of several nature through the skin and the subcutaneous regions of the human being are known, such as acupunture and certain other related sciences, which are in a very incipient stage of research and that, as has been already ascertained, result in various reactions of the individual, achieved through the skin in predetermined well located zones of the human body.

However, up to the present time, no one has ever experimented with the application of light energy of various frequencies on the skin of the human being, and it has been surprisingly found that the application of said light energy, through an optical grid having square frustopyramidal openings, with the points of the grid directed toward said light source, may provide certain stimulations which may be compared, in a certain way, to the stimulations provided by acupunture. Also, by means of the application of certain light frequencies, a germicidal effect is achieved.

BRIEF SUMMARY OF THE INVENTION

It is therefore an object of the present invention to provide an apparatus for applying light energy, which is of very simple construction and yet of unexpected effects as regards the induction of stimulation and other actions in certain skin zones of the human being.

One more object of the present invention is to provide an apparatus of the above mentioned nature, which may use various luminous frequencies and which may operate, for certain particular purposes, in a predetermined vacuum.

One other object of the present invention is to provide an apparatus of the above mentioned character, which may be used for treating fluids to kill germs.

BRIEF DESCRIPTION OF THE DRAWINGS

The novel features that I consider characteristic of my invention are set forth with particularity in the appended claims. The invention itself, however, both as to its organization and its method of operation, together with additional objects and advantages thereof, will best be understood from the following description of certain specific embodiments when read in connection with the accompanying drawings, in which:

Figure 1:
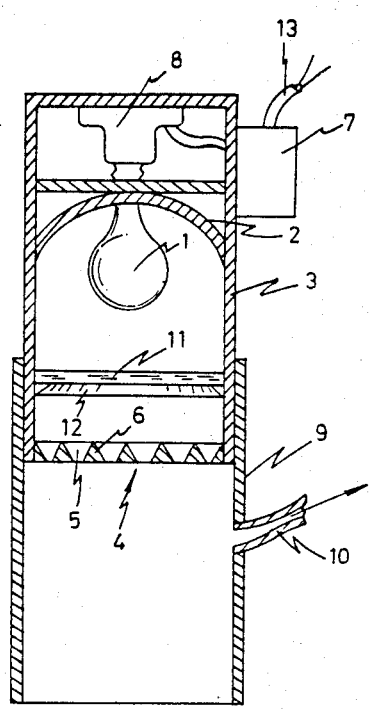
FIG. 1 is a cross-sectional elevational view of a first embodiment of the apparatus built in accordance with the present invention.
Figure 3:
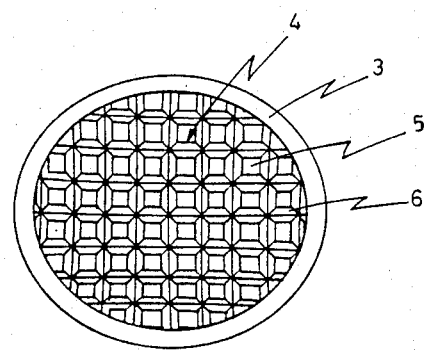
FIG. 3 is a partial view of the apparatus shown in FIGS. 1 and 2, wherein the optical grid contained therein is clearly illustrated.

Having now more particular reference to FIG. 1 of the drawings, there is shown an apparatus in accordance with a first embodiment of the present invention, which comprises a light source 1 supported on a receptacle 8, a reflector 2 surrounding said light source to direct the beams in a suitable direction, a housing 3, on which there is a connection box 7 with its supply cable 13, said housing 3 having an open mouth in which there is supportedly introduced an optical grid 4, built in accordance with copending U.S. patent application Ser. No. 341,019, also filed by the same applicant hereof, and which comprises, such as more clearly illustrated in FIG. 3, two perpendicular sets or bars 6 parallely arranged therebetween and having a triangular cross-section, in order to form a net which leaves square free gaps thereon, such as illustrated under reference numeral 5 in the figures of the drawings, with the points of said bars directed towards the light source such as more clearly illustrated in FIG. 1 of the drawings, and the bases of said bars directed towards the exterior of the housing 3. Said free square gaps constitute openings in the form of truncated square pyramids whose larger base is on the inner face and whose smaller base is on the outer face of the grid, the area of said larger base, with respect to the area of said smaller base, having a ratio of from about 36:1 to 2.25:1, in order to accomplish the desired effects. Optionally, a light filter 11 may be supportedly arranged in the housing 3 by means of a ring 12, between the light source 1 and the optical grid 4, in order to filtrate the light so as to obtain predetermined frequencies. Also, a flexible chamber 9 may be arranged on the open mouth of the housing 3, with a pipe 10 for applying vacuum in order to achieve more remarkable effects.

Figure 2:
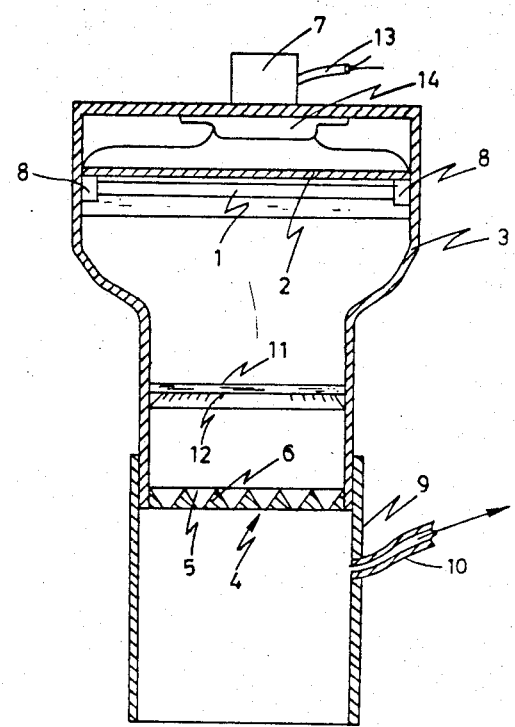
FIG. 2 is a cross-sectional elevational view of a second embodiment.

In FIG. 2, a second embodiment of the apparatus is illustrated, which is identical with the embodiment of FIG. 1, with the exception that a fluorescent tube lamp 1 is used, supported in two end receptacles 8 and connected to a ballast 14, and that the reflector 2 in this particular instance is of semicylindrical form. The housing 3, of course, is of an upwardly flared form in order to accommodate the fluorescent tube 1.

The apparatus of the present invention is highly useful for treating, through the skin of the human being, certain cutaneous, muscular and terminal nervous disorders. Particularly, it has been determined that the application of ultraviolet light produces a remarkable germicidal action which eliminates virus such as Herpes. Other luminous frequencies produce nervous and muscular stimulations which may be used for various therapies.

The device of the present invention is also capable of purifying water in small thicknesses of up to 1 inch, by passing a stream of water through the mouth of the apparatus, in a layer which is not thicker than 1 inch.

Although I have shown and described certain specific embodiments of my invention, I am fully aware that many modifications thereof are possible. My invention, therefore, is not to be restricted except insofar as is necessitated by the prior art and by the spirit of the appended claims.

What I claim is:

1. Apparatus for applying light energy, comprising
   a light source,
   a reflector mounted on one side of said light source, and
   an optical grid mounted on the opposite side of said light source, said optical grid being substantially flat on the side thereof opposite said light source and defining a multiplicity of openings, each of said openings having the shape of a pyramid frustum having square bases and four isosceles trapezoidal sides, the larger of said bases being on the side of said grid towards said light source and the smaller of said bases being on the side of said grid opposite said light source.

2. Apparatus for applying light energy, characterized by comprising in combination a light source, a housing to contain said light source, said housing being formed with an open end, a reflector mounted on one side of said light source and an optical grid arranged as a lid on the open end of said housing and on the side of said light source opposite said reflector, said grid comprising two sets of bars, the bars of one set intersecting the bars of the other set at right angles, each of said bars having a triangular cross section in order to form square frusto-pyramidal openings, with the larger bases of said openings directed towards the inside of the apparatus and the smaller bases of said openings directed towards the outside thereof, and wherein the ratio between the areas of the larger bases and the areas of the smaller bases of said openings is from about 36:1 to about 2.25:1.

3. Apparatus for applying light energy, characterized by comprising in combination a light source, a housing to contain said light source, said housing being formed with an open end, a reflector mounted on one side of said light source and an optical grid arranged as a lid on the open end of said housing and on the side of said light source opposite said reflector, further comprising a light filter arranged between the light source and the optical grid, and a flexible vacuum chamber connected to a vacuum and arranged at the open end of the housing, in order to produce a predetermined vacuum in the area to which the radiation is to be applied.

* * * * *